US012343556B2

(12) United States Patent
Kerns et al.

(10) Patent No.: US 12,343,556 B2
(45) Date of Patent: Jul. 1, 2025

(54) PHOTOTHERAPY DEVICE

(71) Applicant: Lumitex, Inc., Strongsville, OH (US)

(72) Inventors: Michael Kerns, Strongsville, OH (US); Alan Greszler, Strongsville, OH (US); Timothy Orr, Strongsville, OH (US); Dinusha Thotagamuwa, Strongsville, OH (US); Carolyn Guzik, Avon, OH (US)

(73) Assignee: Lumitex, Inc., Strongsville, OH (US)

( * ) Notice: Subject to any disclaimer, the term of this patent is extended or adjusted under 35 U.S.C. 154(b) by 435 days.

(21) Appl. No.: 17/776,679

(22) PCT Filed: Nov. 25, 2020

(86) PCT No.: PCT/US2020/062319
§ 371 (c)(1),
(2) Date: May 13, 2022

(87) PCT Pub. No.: WO2021/108627
PCT Pub. Date: Jun. 3, 2021

(65) Prior Publication Data
US 2022/0395697 A1 Dec. 15, 2022

Related U.S. Application Data

(60) Provisional application No. 62/940,940, filed on Nov. 27, 2019.

(51) Int. Cl.
*A61N 5/06* (2006.01)
(52) U.S. Cl.
CPC .... *A61N 5/0616* (2013.01); *A61N 2005/0626* (2013.01); *A61N 2005/063* (2013.01);
(Continued)

(58) Field of Classification Search
None
See application file for complete search history.

(56) References Cited

U.S. PATENT DOCUMENTS

| 6,537,304 B1* | 3/2003 | Oron | A61N 5/0613 |
| | | | 606/16 |
| 2004/0093042 A1* | 5/2004 | Altshuler | A61B 18/203 |
| | | | 607/88 |

(Continued)

FOREIGN PATENT DOCUMENTS

WO 2017/019482 5/2020

OTHER PUBLICATIONS

International Preliminary Report on Patentability for corresponding PCT application US2020/062319 mailed on May 17, 2022.

*Primary Examiner* — Mallika D Fairchild
(74) *Attorney, Agent, or Firm* — Renner, Otto, Boisselle & Sklar, LLP (57) ABSTRACT

The present disclosure provides a method for treating ischemic stroke by illuminating a skin surface to reduce free radical generation in subsurface target tissues (e.g., the brain following an ischemic event). The method utilizes a waveguide that receives light from a light source. The waveguide is placed adjacent a skin surface of a patient and the waveguide emits light that passes through the skin surface and illuminates a subsurface target tissue. The waveguide includes light-extracting features configured to emit light at a target angle relative to the surface tissue. That is, the light-extracting features alter a trajectory of light emitted by the waveguide, such that a larger percentage of light emitted by the light guide has an angle that is +/-25 degrees off of a center line of the light guide.

21 Claims, 6 Drawing Sheets

(52) U.S. Cl.
CPC .............. *A61N 2005/0645* (2013.01); *A61N 2005/0659* (2013.01); *A61N 2005/0666* (2013.01)

(56) References Cited

U.S. PATENT DOCUMENTS

| | | | |
|---|---|---|---|
| 2006/0116669 A1* | 6/2006 | Dolleris | A61B 18/203 606/17 |
| 2007/0179570 A1* | 8/2007 | De Taboada | A61H 7/006 607/88 |
| 2011/0087311 A1 | 4/2011 | Zorzos et al. | |
| 2011/0295343 A1* | 12/2011 | Bornstein | A61N 5/0624 607/88 |
| 2018/0140172 A1* | 5/2018 | Hu | A61N 5/0622 |

* cited by examiner

PHOTOTHERAPY DEVICE

RELATED APPLICATIONS

This application claims the benefit of PCT/US2020/062319 filed on Nov. 25, 2020; and 62/940,940 filed on Nov. 27, 2019. Which are herein incorporated by reference in their entirety.

TECHNICAL FIELD

The present disclosure relates generally to light emitting apparatus and more particularly to a light emitting apparatus for treating ischemic conditions.

BACKGROUND

Acute ischemic stroke is a common cause of morbidity and mortality worldwide. Acute ischemic stroke is often treated with ischemia-reperfusion (e.g., using revascularization therapy), but this often causes additional trauma due to damage caused by the formation of cytotoxic oxygen-derived free radicals (also called reactive oxygen species (ROS)).

In the damaged ischemic area, the free radicals cause additional cell death (e.g., through protein dysfunction, DNA damage, and lipid peroxidation). Further, free radical damage may also cause hemorrhagic transformation and cerebral edema.

SUMMARY

The majority of reactive oxygen species (ROS) (also referred to as free radicals) are generated in the mitochondria under conditions of cellular stress. For example, studies have shown that ROS are produced at high mitochondrial membrane potentials. In particular, conditions of cellular stress lead to an increase in the activity of cytochrome C oxidase (CcO) through changes in posttranslational modifications of CcO, which causes pathologically high mitochondrial membrane potentials. This in turn leads to excessive ROS production and cell death.

It is possible to reduce CcO activity using light (e.g., infrared light). Consequently, it is possible to reduce mitochondrial membrane potentials (and the associated generation of free radicals) by reducing CcO activity using phototherapy.

The present disclosure provides a method for treating ischemic stroke by illuminating a skin surface (e.g., the scalp) to reduce free radical generation in subsurface target tissues (e.g., the brain following an ischemic event). The method utilizes a waveguide that receives light from a light source. The waveguide is placed adjacent a skin surface of a patient and the waveguide emits light that passes through the skin surface and illuminates a subsurface target tissue. Because light incident on the skin surface having an angle outside of +/−25° from the perpendicular may have difficulty passing through the upper skin layer of the patient to reach the underlying subsurface target tissues, the waveguide includes light-extracting features configured to emit light at a target angle (e.g., approximately perpendicular) to the surface tissue. That is, the light-extracting features alter a trajectory of light emitted by the waveguide, such that a larger percentage of light emitted by the light guide has an angle that is +/−25 degrees off of a center line of the light guide.

In one embodiment, the present disclosure provides a deep tissue (e.g., brain, cardiac, etc.), non-invasive phototherapy treatment to aid in recovery from ischemic events (e.g., stroke, cardiac arrest) using a photobiomodulation mechanism to throttle the tissue's natural recovery mechanism of flooding the area with ROS or free radicals (this natural recovery mechanism is underdamped and is toxic to the tissues brain due to unnecessarily high oxygen levels).

While a number of features are described herein with respect to embodiments of the invention; features described with respect to a given embodiment also may be employed in connection with other embodiments. The following description and the annexed drawings set forth certain illustrative embodiments of the invention. These embodiments are indicative, however, of but a few of the various ways in which the principles of the invention may be employed. Other objects, advantages, and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention in which similar reference numerals are used to indicate the same or similar parts in the various views.

The present invention is now described in detail with reference to the drawings. In the drawings, each element with a reference number is similar to other elements with the same reference number independent of any letter designation following the reference number. In the text, a reference number with a specific letter designation following the reference number refers to the specific element with the number and letter designation and a reference number without a specific letter designation refers to all elements

DETAILED DESCRIPTION

The present invention provides a phototherapy apparatus including a wave guide for receiving light from a light source and for controlling a trajectory of light emitted by the wave guide, such that an angle of the emitted light relative to a surface falls within a predetermined angular range.

Figure 1:
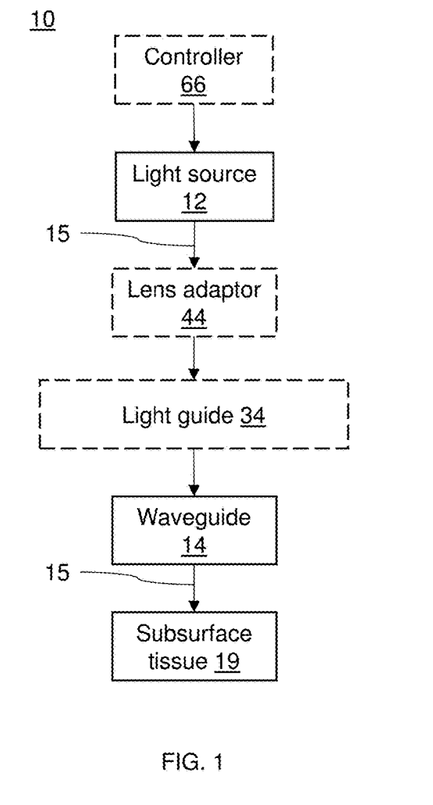
FIG. 1 is a block diagram of a first embodiment of a phototherapy apparatus.
Figure 2:
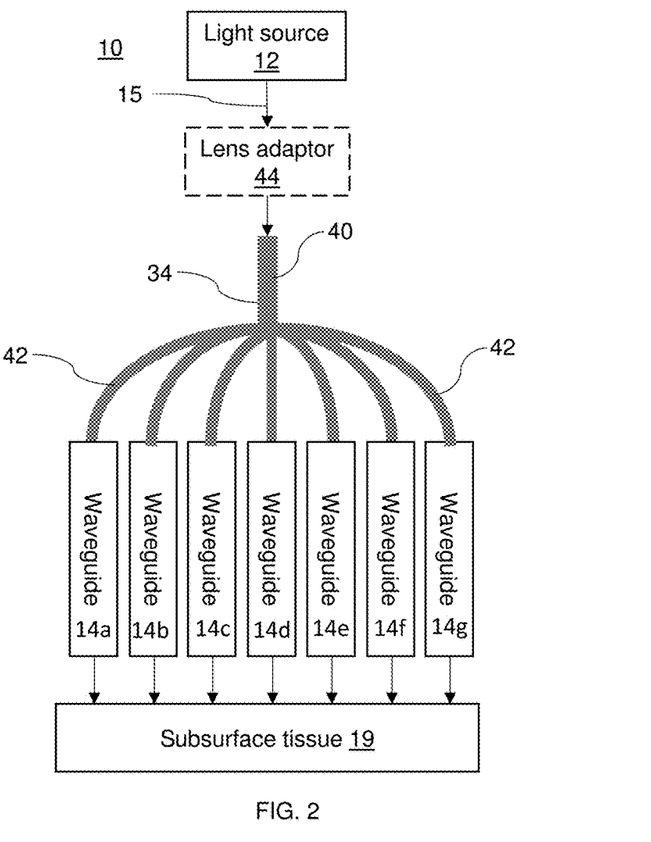
FIG. 2 is a block diagram of a second embodiment of a phototherapy apparatus.

In the embodiments shown in FIGS. 1 and 2, the phototherapy apparatus 10 includes a light source 12 and at least one waveguide 14. The waveguides 14 receive electromagnetic radiation (also referred to as light) 15 from the light source 12 at a light receiving surface 16 of each of the waveguides 14. Each of the waveguides 14 emit light 15 from a light emitting surface 18 towards a subsurface target tissue 19. The light 15 is extracted from the waveguides 14 using light-extracting features 22 configured to extract the light, such that at least 50% of the light 15 emitted from the light emitting surface 18 is within ten degrees of a target angle to the light emitting surface 18. Each of the waveguides 14 is made of a biocompatible material having a hardness of 50 shore A or less.

The light 15 from the light source 12 may be emitted omnidirectionally. As shown in the embodiments depicted in FIGS. 3 and 4, the waveguide (also referred to as a light directing structure) 14 redirects the received light 15, such that an angle of the redirected light relative to the light emitting surface 18 and the surface tissue 32 falls within a predetermined range. For example, the light may be emitted by the waveguide 14, such that at least 70% of the emitted light interacts with the surface 32 at an angle of +/−25° from perpendicular to the surface tissue 32. In the embodiment shown in FIG. 3, the light 15 emitted by the light emitting surface 18 is centered around the target angle of approximately 40° relative to the skin surface and a majority of the emitted light 15 is contained within ten degrees of the target angle. The target angle may be any suitable angle. For example, the target angle may be approximately perpendicular to the skin surface 32 (i.e., zero degrees). As another example, the target angle may be any angle between 0 and forty degrees relative to the skin surface 32.

Figure 3:
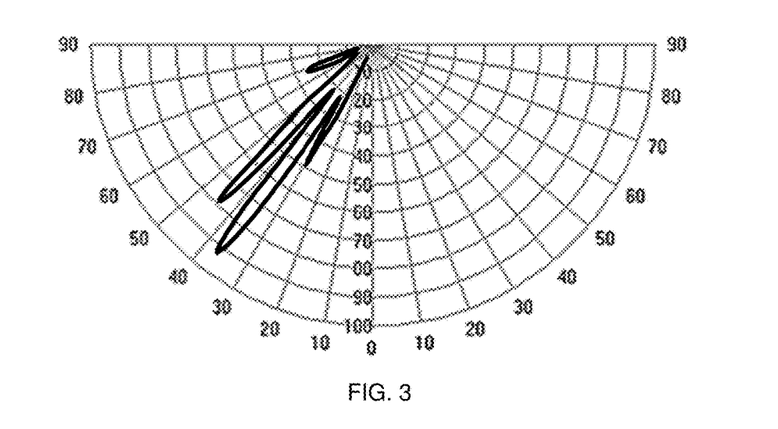
FIG. 3 is a polar candela distribution plot depicting an exemplary distribution of light exiting a waveguide.
Figure 4:
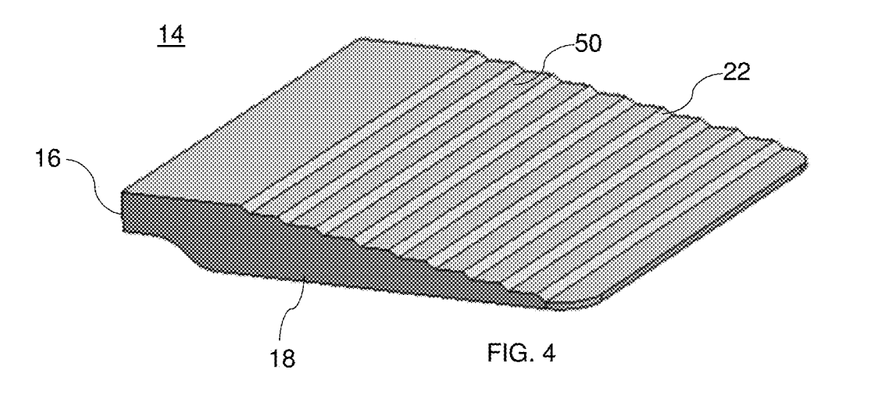
FIG. 4 is a top perspective view of an exemplary waveguide of the phototherapy apparatus.

In one embodiment, pressure is applied to the waveguides 14 to ensure that the light emitting surface 18 is adjacent the skin surface 32. This may improve light reaching the target tissue 19 by reducing index of refraction boundaries (i.e., a waveguide 14 to skin surface 32 boundary instead of both a waveguide 14 to air boundary and an air to skin surface 32 boundary). Additionally, the light emitting surface 18 being adjacent the skin surface 32 helps ensure that the light emitted in the preferred angular range from the light emitting surface 18 interacts with the skin surface 32 in the same preferred angular range. Any gaps between the light emitting surface 18 and the skin surface 32 may alter the angle that the emitted light 15 interacts with the skin surface 32. A softness of the waveguide 14 may depend on properties of the skin surface 32 and/or the target tissue 19. For example, the waveguide 14 softness may be sufficient for the waveguide 14 to conform to a contour of the skin surface 19 (e.g., a radius of curvature R may be 50 mm for a skull).

The waveguides 14 may be any suitable object for receiving light and directing light towards the subsurface target tissue 19. In one example, the waveguides 14 are made from silicone, urethane, polyethylene, or any material having a hardness of 50 shore A or softer. The waveguides 14 may be flexibly molded, rigid, machined to match the contour of the surface tissue, 3D printed, refractive, diffractive, a lens, a light guide, a fiber (e.g., circular or flat), woven fiber, Uniglo, etc. A portion of the waveguide 14 including the light emitting surface 18 may have a hardness of 50 shore A or less to mitigate tissue damage that may be caused by more rigid structures.

In another embodiment, the waveguide 14 is at least semi-rigid (having a hardness of greater than 50 shore A) and the light emitting surface 18 may have a curvature that conforms to a curvature of the surface tissue 19. In still another embodiment, the waveguide 14 includes a rigid portion (having a hardness of greater than 50 shore A) and a flexible portion (having a hardness of less than 50 shore A). The rigid portion has a curvature that conforms to a curvature of the surface tissue 19. The flexible portion is located adjacent the rigid portion, and is configured to be positioned between the rigid portion and the surface tissue 19.

In the embodiment shown in FIG. 4, the light-extracting features 22 include at least one of a shape of a reflective surface 50 of each of the waveguides 14 located opposite the light emitting surface 18; lensing features on the light emitting surface 18; or a texturing of the light emitting surface 18. As described above, a preferred angle may be +/−ten degrees from the target angle with greater than 50% of the emitted light 15 falling within this angular range. In another embodiment, at least 70% or at least 80% of the emitted light 15 falls within this angular range. In still another embodiment, at least 50%, at least 70%, or at least 80% of the emitted light 15 falls within an angular range of +/−five degrees of the target angle.

Figure 5:
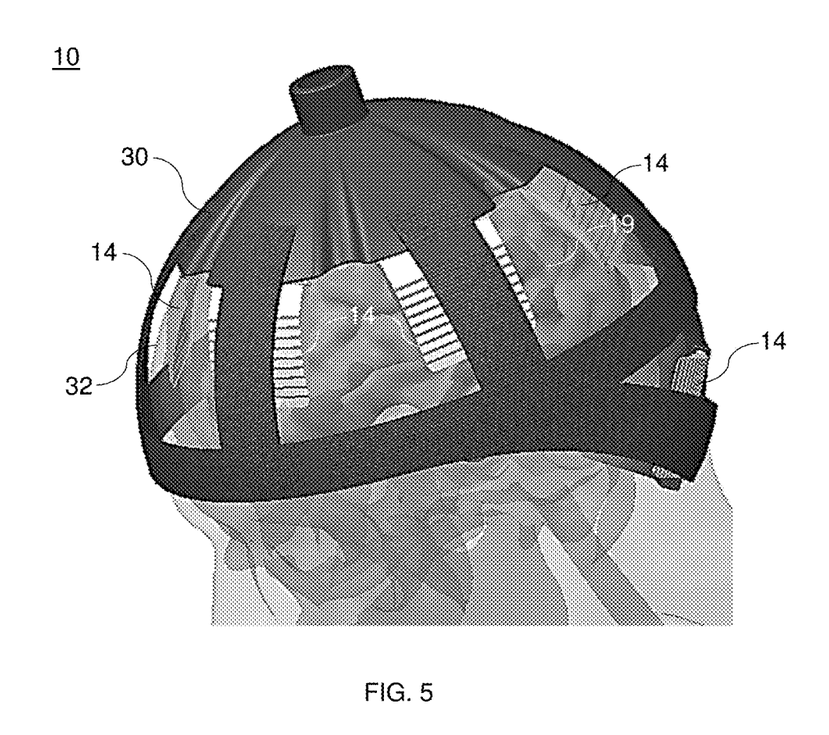
FIG. 5 is a perspective view of a phototherapy apparatus including a housing.
Figure 6:
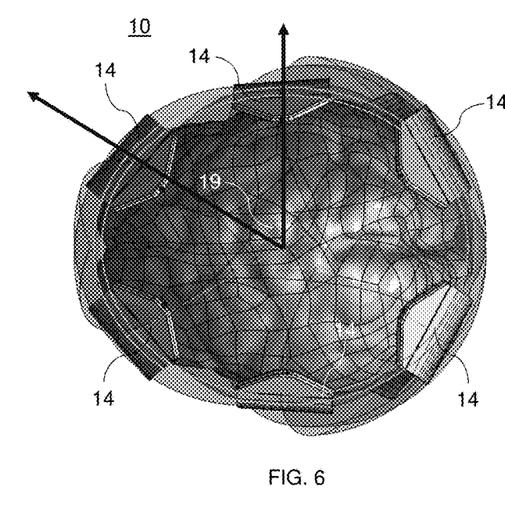
FIG. 6 is a top perspective view of a phototherapy apparatus positioned on a skull of a patient.
Figure 7:
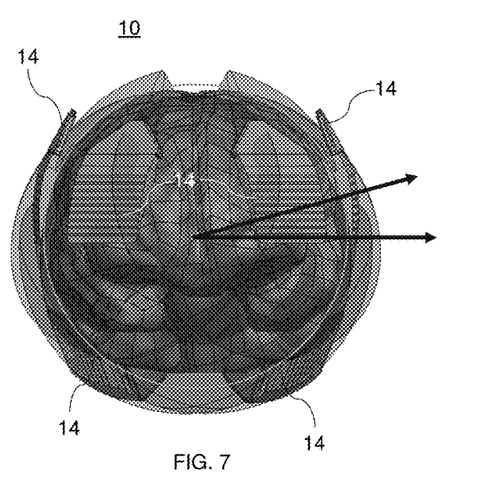
FIG. 7 is a rear perspective view of the phototherapy apparatus of FIG. 6.

As shown in FIGS. 5-7, the phototherapy system 10 may include any suitable number of waveguides 14. For example, the phototherapy system 10 may include seven waveguides. The number of waveguides 14 may depend on the target tissue 32 and the properties of the patient. For example, the subsurface target tissues 19 may include at least one of brain tissue, cardiac tissue, prostate tissue, or pulmonary tissue. To illuminate pulmonary tissue of an adult, twenty waveguides 14 may be used. However, illuminating brain tissue of an infant may use seven waveguides 14.

In the embodiment shown in FIG. 5, the phototherapy system 10 includes a housing 30. The housing 30 maintains a position of the waveguides 14 adjacent to surface tissue 32 and presses the light emitting surface 18 of the waveguides 14 against the surface tissue 32, such that the light emitting surface 18 conforms to a curvature of the surface tissue 32.

The housing 30 may be any suitable structure for pressing the waveguides 14 against the surface tissue 32. For example, the housing 30 may be an elastic band and/or may be adjustable to increase or decrease the pressure applied to the waveguides 14. In the embodiment shown in FIG. 5, the housing 30 is shaped to hold waveguides 14 against a head of a patient. In another embodiment, the housing 30 may be used to hold the waveguides 14 against a chest of a patient to illuminate a heart and/or lungs of the patient.

The phototherapy system 10 shown in FIG. 5 may be a head-worn system used to apply emergency treatment to ischemic newborns (e.g., when the cord is wrapped around neck) or used to treat adult stroke. In another embodiment, the phototherapy system 10 may be a bandage type system for aiding surgical wound healing or for cardiac arrest patients. The phototherapy system 10 is not limited to treating ischemic events, but may be used to apply phototherapy to any suitable tissue. For example, the subsurface target tissue 19 may be endocrine tissue (e.g., located outside of the prostate), peripheral nervous tissue, gastrointestinal tissue, skeletal muscle, etc.

The housing 30 may include radially emitting glass fiber integrated into the structure of the housing (e.g., possibly woven) to deliver light to the subsurface target tissue (also referred to as the target region). That is, the waveguide 14 may be woven into the housing 30.

In the embodiment shown in FIGS. 1 and 2, the phototherapy system 10 includes a light guide 34. The light guide 34 is configured to receive the light 15 from the light source 12 and to deliver the light 15 to the light receiving surface 16 of the waveguide 14. In the embodiment shown in FIG. 2, the light guide 34 includes a unitary proximal portion 40 that receives the light 15 from the light source 12. The unitary proximal portion 40 branches into multiple branching portions 42 and each of the multiple branching portions 42 terminate in an associated waveguide 14. Each of the multiple branching portions 42 delivers the light 15 from the light source 12 to the associated waveguide 14.

The waveguide 14 may comprise a separate component from the light guide 12 and/or a coating or an overmolding of the light guide 12. For example, the light guide 12 may include multiple branches as shown in FIG. 2. The waveguide 14 may comprise a separate component including channels for receiving the different branches of the light guide 12. In another example, the light guide 12 may include a woven component (e.g., the light guide may include fiber optics that are woven together). In this example, the waveguide 14 may be applied as a coating of the light guide 12 or the waveguide 14 may be applied to the light guide 12 by overmolding the waveguide 14 onto the light guide 12.

The waveguide 14 may alter the trajectory of the light 15 emitted by the light guide 12 through total internal reflection. That is, the emitted light may reflect at a surface of the light directing structure 14 due to a difference in index of refraction. Alternatively or additionally, the light directing structure 14 may also include a reflective layer 50 configured to reflect the emitted light.

In the embodiments shown in FIGS. 1 and 2, the phototherapy system 10 may include a lens adapter 44. The lens adapter 44 receives the light 15 from the light source 12 and alters a trajectory of the received light 15, such that a percentage of the light 15 from the light source 12 that is received by the light guide 34 is improved (e.g., compared to if the lens adapter 44 was not included). For example, the light source 12 may include multiple light emitters emitting different wavelengths of light. The light source 12 may be integrated into an adaptor lens 44 that directs the light 15 into the light guide 34 or waveguide 14. For example, the lens adapter 44 may be a plano-convex lens housed in a tube. The lens may include an anti-reflective coating and may be able to be applied dry or with a film of an index matching gel to aid in tissue penetration.

The light source 12 may be any source of light. For example, the light source 12 may be an external light box mechanically separated from the waveguides 14 and optically coupled to the waveguides via the light guide 34. In one example, the light source 12 is not physically supported by the waveguides 34, but is instead supported by an external structure such as a table. In one embodiment, the light source 12 is an external light box including a laser light emitter (e.g., externally located with an optical cable to optically couple the light source and the waveguide).

The light 15 emitted by the light source 12 may have any suitable properties. The light source 12 may include any wavelength of electromagnetic radiation (also referred to as light). For example, the light source 12 may emit light including at least one of 9040 nm or 750 nm. In one embodiment, the light source 12 is a 30 W 940 nm multi-mode fiber coupled laser system and a 20 W 750 nm multi-mode fiber coupled laser module. the light source may emit different wavelengths of light sequentially or simultaneously.

In one embodiment, the light source 12 includes a 940 nm source having a 105 µm core glass fiber and a 750 nm system having a 400 µm core glass fiber. Each light emitter is coupled to a 1-to-7 fused fiber bundle (i.e., the light guide 34) via a lens adaptor 44. All connections may be made with an industry standard connector SMA-905.

Figure 8:
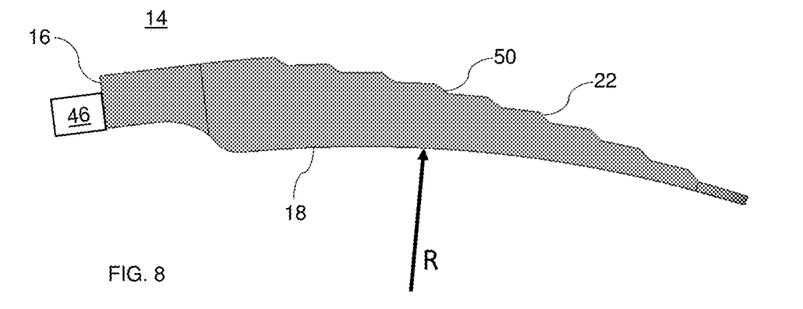
FIG. 8 is a side view of the waveguide of FIG. 3 bent to conform to a curved surface.
Figure 9:
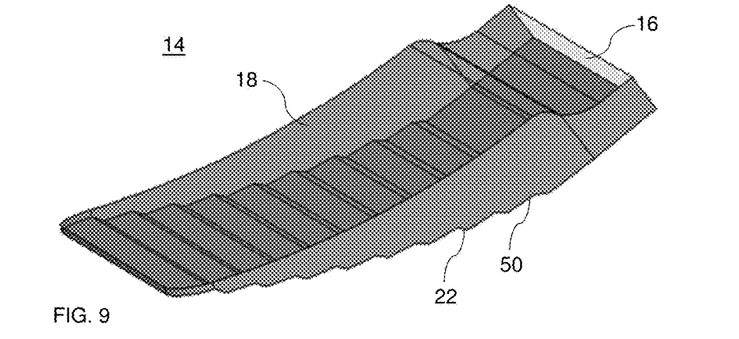
FIG. 9 is a transparent bottom perspective view of the waveguide of FIG. 8.

In one embodiment, the light source 12 includes multiple light emitters 46 physically attached to the waveguides 14. For example, as shown in FIG. 8, each waveguide 14 may include one or more light emitters 46 that are attached to or physically supported by the waveguide 14. The light emitter(s) 14 may be attached to the waveguide 14 include any suitable method. For example, each waveguide 14 may include a light emitter 46 that is adhered to the waveguide 14. The light emitter 46 may emit light through the adhesive and into the waveguide 14. In another embodiment, the phototherapy system 10 includes cluster(s) of LEDs located within a wearable structure with an optical interface.

The light emitters 46 may be any suitable structure for emitting light. For example, the light emitters 46 may include one or more light emitting diodes (LEDs), organic LEDs (OLEDs), microLEDs, laser diodes, mini-LED, quantum dot (QD)-conversion, phosphor conversion, excimer lamps, multi-photon combination, or SLM wavefront manipulation.

Figure 10:
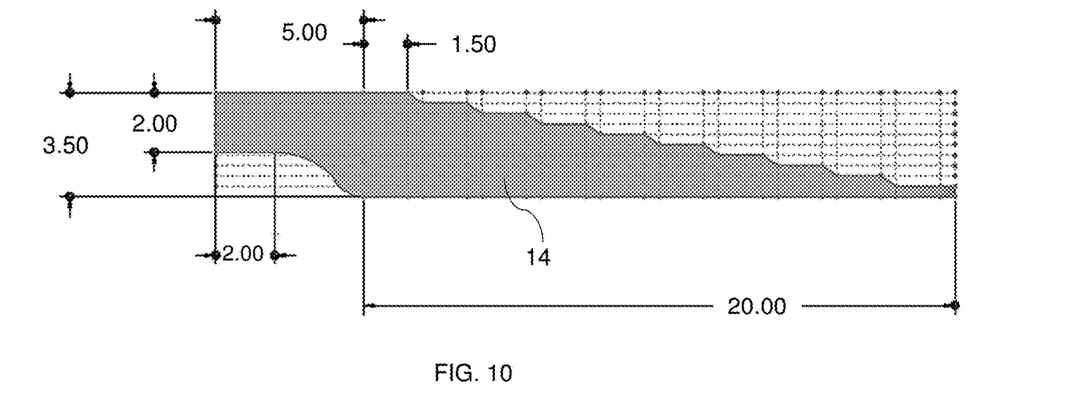
FIG. 10 is a side view of an exemplary waveguide including measurements.
Figure 11:
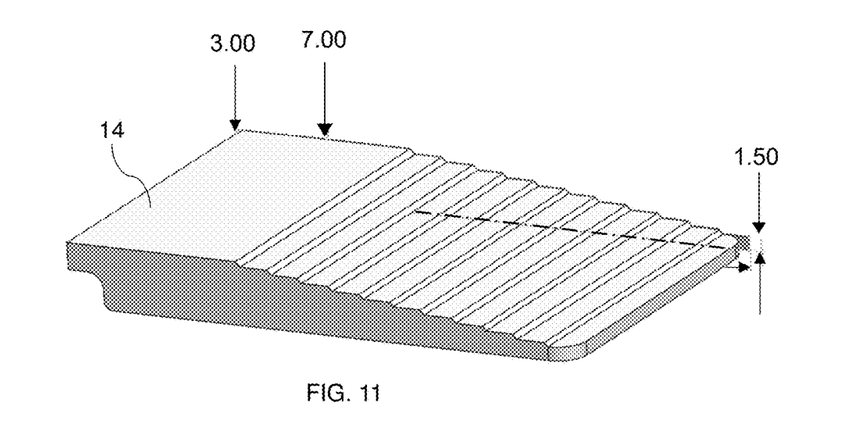
FIG. 11 is a top perspective view of another exemplary waveguide including measurements.

In the embodiment depicted in FIGS. 10 and 11, dimensions of an exemplary waveguide are provided. The depicted waveguide may be used for illuminating brain tissue.

Figure 12:
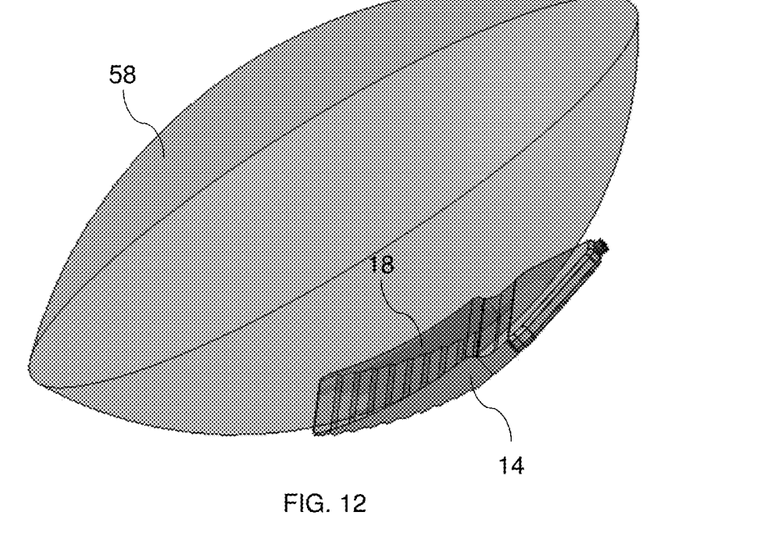
FIG. 12 is a bottom perspective view of a waveguide and a volume of tissue illuminated by the waveguide.
Figure 13:
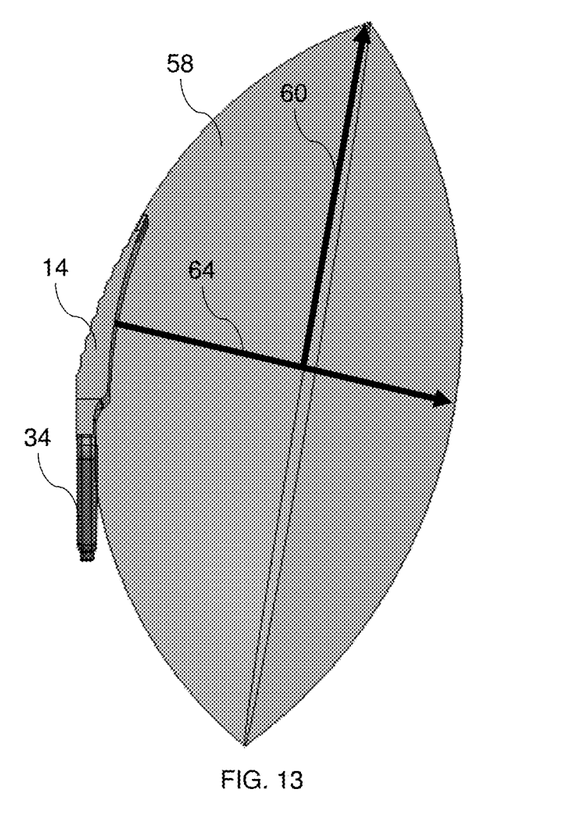
FIG. 13 is a side perspective view of the waveguide and the volume of tissue of FIG. 12.

The volume of tissue illustrated in FIGS. 12 and 13 represents the volume 58 of tissue that receives the minimum therapeutic fluence value (e.g., 50 µW). Line 60 indicates a direction of radial scatter in the tissue 58. Similarly, line 62 indicates a direction of a maximum depth of transmission.

The phototherapy apparatus 10 may be used in a method to treat an ischemic event. For example, the light guide 12 may be placed adjacent to a skin surface of the patient at a location close to the ischemic event. As an example, the light guide 12 may be placed such that the emitted light illuminates the scalp of a patient that has experienced a cerebral stroke. In this way, light emitted by the phototherapy apparatus 10 may reduce the production of free radicals near and in the brain, reducing the number of free radicals in the ischemic area(s) of the brain.

Figure 14:
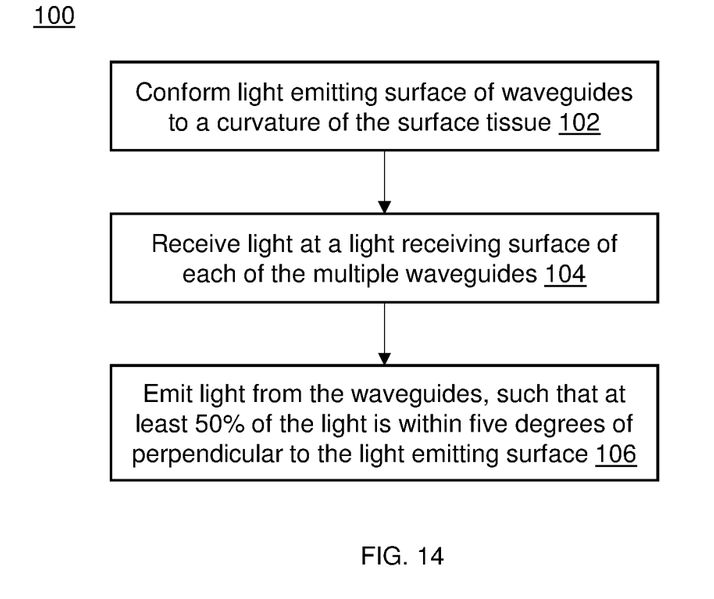
FIG. 14 is an embodiment of a method for providing phototherapy by illuminating a subsurface target tissue below a surface tissue.

Turning to FIG. 14, an embodiment of a method 100 is shown for providing phototherapy by illuminating a subsurface target tissue 19 below a surface tissue 32. In process block 102, a light emitting surface 18 of each waveguide 14 is conformed to a curvature of the surface tissue 32 by pressing each of the waveguides 14 against the surface tissue 32. In process block 104, light 15 from a light source 12 is received at a light receiving surface 16 of each of the waveguides 14. In process block 106, the light 15 is emitted from a light emitting surface 18 of each waveguide 14 by extracting the light using light-extracting features 22, such that at least 50% of the light emitted from the light emitting surface is within ten degrees of the target angle relative to the light emitting surface.

In one embodiment, the phototherapy system 10 includes a sensor or user input for determining a size of a target volume. A controller 66 included in the phototherapy system 10 may modulate the optical power output by the light source 12 based on the target area size to target a specific power density. For example, the sensor may be used to measure the size of the target volume may be an electronic strain sensor, FBG optical strain sensor, machine vision system, or air pressure monitor (i.e., for performing a volumetric measurement).

The controller 66 may have various implementations. For example, the controller 66 may include any suitable device, such as a processor (e.g., CPU), programmable circuit, integrated circuit, memory and I/O circuits, an application specific integrated circuit, microcontroller, complex programmable logic device, other programmable circuits, or the like. The controller 66 may also include a non-transitory computer readable medium, such as random-access memory (RAM), a read-only memory (ROM), an erasable programmable read-only memory (EPROM or Flash memory), or any other suitable medium. Instructions for performing the method described below may be stored in the non-transitory computer readable medium and executed by the controller 66. The controller 66 may be communicatively coupled to the computer readable medium and network interface through a system bus, mother board, or using any other suitable structure known in the art.

The phototherapy system 10 may also include a sensor for sensing optical power. The sensor may be located at the skin surface 32 (e.g., the head) and/or within the light source 12. The sensor may be used as part of a closed loop system to regulate the power supplied to the light source 12, such that the optical power being delivered to the target tissue 19 falls within a predetermined range. For example, the sensor may be a photodiode, SiPM, camera, or spectrometer. The controller 66 may control the light source 12 based on the sensed optical power, such that the target tissue 19 receives a predetermined optical dose. For example, the predetermined optical dose may be an amount of light known to cause a physiological effect.

The phototherapy system 10 may also include a sensor (e.g., a thermometer) for measuring skin temperature at the tissue surface 32. The controller 66 may receive the measured skin temperature and modulate optical power output by the phototherapy system 10, such that the skin temperature stays below a threshold (i.e., to avoid overheating). The sensor may be any suitable sensor for measuring temperature, such as a thermometer, infrared camera/photodiode, spectrometer, etc. The sensor may be embedded in LDU, mounted on the target tissue, or used to measure air temperature.

The controller 66 may also be configured to pulse width modulate the light source 12. The controller 66 may also control a duty cycle of the light source 12 to improve penetration of the light 15 into the tissue and/or to modulate a temperature of the skin. The controller 66 may similarly modulate the frequency of emitted light 15 to improve tissue penetration.

An interface material may be applied to the surface tissue 32 as an interface to the body. The interface material may be thermal conductive and mediate skin temperature. The interface material may be index matching to enhance optical coupling. The interface material may be used to mechanically cushion the tissue and/or to adhere to the surface tissue.

The phototherapy system 10 may also include a mask for controlling illumination of the tissues. For example, the mask may be an elastic mesh having cutouts that fit to the target tissue 19. The mask may be thermally conductive, light reflective, light absorbing, a diffuse scatterer, and/or light tight.

The phototherapy system 10 may also include features designed to effect different human factors. For example, anything auxiliary to the actual performance of device meant to improve the human experience using it. As examples, mood affecting ambient lighting, sounds, graphics, etc.

All ranges and ratio limits disclosed in the specification and claims may be combined in any manner. Unless specifically stated otherwise, references to "a," "an," and/or "the" may include one or more than one, and that reference to an item in the singular may also include the item in the plural.

Although the invention has been shown and described with respect to a certain embodiment or embodiments, equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A phototherapy system for illuminating a subsurface target tissue below a surface tissue, the phototherapy system including:
   a light source configured to emit light;
   multiple waveguides configured to:
      receive the light from the light source at a light receiving surface of each of the multiple waveguides; and
      emit light from a light emitting surface of each of the multiple waveguides;
   wherein each of the multiple waveguides includes:
      the light emitting surface on a first side of the waveguide;
      a reflective surface on a second side of the waveguide located opposite the light emitting surface on the first side of the waveguide;
      a first lateral edge extending between the reflective surface on the second side and the light emitting surface on the first side;
      a second lateral edge opposite the first lateral edge and extending between the reflective surface on the second side and the light emitting surface on the first side;
      a tapered edge located opposite the light receiving surface and extending between the first lateral edge and the second lateral edge; and
      light-extracting features configured to extract light from the waveguide, such that at least 50% of the light emitted from the light emitting surface is within ten degrees of a target angle to the light emitting surface;
   wherein the light-extracting features of each of the multiple waveguides include a shape of the second side of the waveguide such that the reflective surface forms multiple tapered stair steps between the light emitting surface and the tapered edge, such that a thickness of the waveguide extending between the reflective surface and the light emitting surface decreases from the light receiving surface to the tapered edge; and wherein each of the multiple waveguides is made of a biocompatible material having a hardness of 50 shore A or less.

2. The phototherapy system of claim 1, further comprising a housing, wherein the housing is configured to maintain a position of the multiple waveguides adjacent the surface tissue and to press the light emitting surface of each of the multiple waveguides against the surface tissue, such that the light emitting surface of each of the multiple waveguides conforms to a curvature of the surface tissue.

3. The photo therapy system of claim 1, further comprising a light guide configured to receive the light from the light source and deliver the light to the light receiving surface of the waveguide.

4. The phototherapy system of claim 3, wherein:
the light guide includes a unitary proximal portion that receives the light from the light source;
the unitary proximal portion branches into multiple branching portions and each of the multiple branching portions terminates in an associated waveguide of the multiple waveguides; and
each of the multiple branching portions delivers the light from the light source to the associated waveguide.

5. The phototherapy system of claim 3, further comprising a lens adapter configured to receive the light from the light source and to alter a trajectory of the received light to improve a percentage of the light from the light source that is received by the light guide.

6. The phototherapy system of claim 4, wherein the light source is an external light box mechanically separated from the multiple waveguides and optically coupled to the multiple waveguides via the light guide.

7. The phototherapy system of claim 1, wherein the light source includes multiple light emitters physically attached to the waveguides.

8. The phototherapy system of claim 7, wherein the multiple light emitters are light emitting diodes (LEDs).

9. The phototherapy system of claim 1, wherein the multiple waveguides include at least seven waveguides.

10. The phototherapy system of claim 1, wherein the light-extracting features additionally include at least one of lensing features on the light emitting surface or a texturing of the light emitting surface.

11. The phototherapy system of claim 1, wherein the subsurface target tissues include at least one of brain tissue, cardiac tissue, prostate tissue, or pulmonary tissue.

12. The phototherapy system of claim 1, wherein the light has a wavelength range and the wavelength range includes at least one of 940 nm and 750 nm.

13. The phototherapy system of claim 1, further comprising an index matching gel configured to be placed between and adjacent to both the surface tissue and the light emitting surface.

14. The phototherapy system of claim 1, further comprising a sensor and a controller, wherein:
the controller is configured to receive a signal from the sensor and to modulate the light emitted by the light source based on the received signal.

15. The phototherapy system of claim 14, wherein:
the sensor is configured to output the signal based on a sensed temperature; and
when the signal indicates the sensed temperature is above a temperature threshold, the controller is configured to reduce a fluence of the light emitted by the light source.

16. The phototherapy system of claim 14, wherein:
the sensor is configured to output the signal based on a sensed optical power; and
the controller is configured to control the light source based on the sensed optical power, such that the subsurface target tissue receives a predetermined optical dose.

17. A waveguide for illuminating a subsurface target tissue below a surface tissue with light from a light source, the waveguide including:
a light receiving surface configured to receive the light from the light source;
a light emitting surface on a first side of the waveguide configured to emit the received light;
a reflective surface on a second side of the waveguide located opposite the light emitting surface on the first side of the waveguide;
a first lateral edge extending between the reflective surface on the second side and the light emitting surface on the first side;
a second lateral edge opposite the first lateral edge and extending between the reflective surface on the second side and the light emitting surface on the first side;
a tapered edge located opposite the light receiving surface and extending between the first lateral edge and the second lateral edge; and
light-extracting features configured to extract light from the waveguide, such that at least 50% of the light emitted from the light emitting surface is within ten degrees of a target angle to the light emitting surface;
wherein the light-extracting features of include a shape of the second side of the waveguide such that the reflective surface forms multiple tapered stair steps between the light emitting surface and the tapered edge, such that a thickness of the waveguide extending between the reflective surface and the light emitting surface decreases from the light receiving surface to the tapered edge; and
wherein the waveguide is made of a biocompatible material having a hardness of 50 shore A or less.

18. The waveguide of claim 17, wherein the light emitting surface of the waveguide conforms to a curvature of the surface tissue when pressed against the surface tissue.

19. The waveguide of claim 17, wherein the light-extracting features include at least one of lensing features on the light emitting surface or a texturing of the light emitting surface.

20. A method of providing phototherapy by illuminating a subsurface target tissue below a surface tissue, the method including:
conforming a light emitting surface of each of multiple waveguides to a curvature of the surface tissue by pressing each of the waveguides against the surface tissue, wherein each of the multiple waveguides is made of a biocompatible material having a hardness of 50 shore A or less;
receiving light from a light source at a light receiving surface of each of the multiple waveguides, wherein each of the multiple waveguides includes:
the light emitting surface on a first side of the waveguide;
a reflective surface on a second side of the waveguide located opposite the light emitting surface on the first side of the waveguide;
a first lateral edge extending between the reflective surface on the second side and the light emitting surface on the first side;

a second lateral edge opposite the first lateral edge and extending between the reflective surface on the second side and the light emitting surface on the first side;

a tapered edge located opposite the light receiving surface and extending between the first lateral edge and the second lateral edge; and emitting the light from a light emitting surface of each of the multiple waveguides by extracting the light from each of the waveguides using light-extracting features of each of the multiple waveguides, such that at least 50% of the light emitted from the light emitting surface is within ten degrees of a target angle to the light emitting surface;

wherein the light-extracting features of each of the multiple waveguides include a shape of the second side of the waveguide such that the reflective surface forms multiple tapered stair steps between the light emitting surface and the tapered edge, such that a thickness of the waveguide extending between the reflective surface and the light emitting surface decreases from the light receiving surface to the tapered edge.

21. The phototherapy system of claim 1, wherein:

each stair step of the multiple tapered stair steps:
  is located adjacent to another stair step of the multiple tapered stair steps; and
  includes a descending ramped portion followed by a flat portion;

adjacent stair steps of the multiple tapered stair steps comprise an initial stair step and a latter stair step; and for adjacent stair steps:
  the flat portion of the initial stair step physically connects to the descending ramped portion of the latter stair step; and
  the initial stair step is located closer to the light receiving surface than the latter stair step.

* * * * *